(12) United States Patent
Wehrle et al.

(10) Patent No.: US 6,596,918 B1
(45) Date of Patent: Jul. 22, 2003

(54) ABSORBENT ARTICLES HAVING WETNESS INDICATING GRAPHICS AND EMPLOYING MASKING TECHNIQUES

(75) Inventors: Richard Thomas Wehrle, New London, WI (US); Ryan James McEnenany, Appleton, WI (US); Christopher Peter Olson, Neenah, WI (US); Joseph Earl Pierce, Appleton, WI (US); Kathleen Irene Ratliff, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 110 days.

(21) Appl. No.: 09/587,002

(22) Filed: Jun. 5, 2000

(51) Int. Cl.[7] ................................ A61F 13/15
(52) U.S. Cl. ........................ 604/361; 604/364
(58) Field of Search ................ 604/361, 364, 604/385.01, 385.21, 385.23, 386, 396; 115/200, 206, 207, 211, 216; 128/886

(56) References Cited

U.S. PATENT DOCUMENTS

| | | |
|---|---|---|
| 2,787,238 A | 4/1957 | Luce |
| 3,004,895 A | 10/1961 | Schwartz |
| 3,675,654 A | 7/1972 | Baker et al. |
| 3,702,610 A | 11/1972 | Sheppard et al. |
| 3,759,261 A | 9/1973 | Wang |
| 3,898,172 A | 8/1975 | Reif et al. |
| 3,918,454 A | 11/1975 | Korodi et al. |
| 3,952,746 A | 4/1976 | Summers |
| 4,022,211 A * | 5/1977 | Timmons et al. ........... 128/287 |

(List continued on next page.)

FOREIGN PATENT DOCUMENTS

| | | |
|---|---|---|
| DE | 3810473 A1 | 10/1989 |
| EP | 0021492 A1 | 1/1981 |
| EP | 0148115 A1 | 7/1985 |
| EP | 0203715 A2 | 12/1986 |
| EP | 0217032 A2 | 4/1987 |
| EP | 0286543 A2 | 10/1988 |
| EP | 0776645 A1 | 6/1997 |
| EP | 0813850 A2 | 12/1997 |
| FR | 2541872 A3 | 9/1984 |
| FR | 2559037 A1 | 8/1995 |
| GB | 2022423 A | 12/1979 |
| JP | 58174601 A | 10/1983 |
| JP | 1075980 A | 3/1989 |
| JP | 9140742 | 6/1997 |
| WO | WO 8604219 A1 | 7/1986 |
| WO | WO 8700945 A1 | 2/1987 |
| WO | WO 9500099 A1 | 1/1995 |
| WO | WO 00/35401 | 6/2000 |
| WO | WO 00/76438 A2 | 12/2000 |
| WO | WO 00/76443 A1 | 12/2000 |
| WO | WO 01/21126 | 3/2001 |

OTHER PUBLICATIONS

Patent Abstracts of Japan 10108877 A: Description of Uni Charm Corp., "Disposable Diaper of Briefs Type.".
Patent Abstracts of Japan 11104172 A: Description of Uni Charm Corp., "Disposable Pants Type Diaper.".
Patent Abstracts of Japan 2000000266 A: Description of Oji Paper Co. Ltd., "Printing of Absorptive Wearing Article and Absorptive Wearing Article Subjected to Printing".
Patent Abstracts of Japan 2001170108 A2: Description of Crecia Corp., "Perfect Brief–Shaped Paper Diaper.".

*Primary Examiner*—Weilun Lo
*Assistant Examiner*—Jacqueline F Stephens
(74) *Attorney, Agent, or Firm*—Thomas M. Gage; H. Michael Kubicki (57) ABSTRACT

A disposable absorbent article such as a training pant includes a liquid soluble wetness indicator and one or more, masking techniques for minimizing the likelihood of smudges appearing after activation. The techniques include masking graphics and peripherally disposed adhesive patterns.

26 Claims, 6 Drawing Sheets

U.S. PATENT DOCUMENTS

| | | | |
|---|---|---|---|
| 4,192,311 A | 3/1980 | Felfoldi | |
| 4,231,370 A | 11/1980 | Mroz et al. | |
| 4,249,532 A | 2/1981 | Polansky et al. | |
| 4,287,153 A | 9/1981 | Towsend | |
| 4,292,916 A | 10/1981 | Bradley et al. | |
| 4,327,731 A | 5/1982 | Powell | |
| 4,507,121 A | 3/1985 | Leung | |
| 4,581,772 A | 4/1986 | Smith | |
| 4,662,875 A | 5/1987 | Hirotsu et al. | |
| 4,663,220 A | 5/1987 | Wisneski et al. | |
| 4,704,116 A | 11/1987 | Enloe | |
| 4,705,513 A | 11/1987 | Sheldon et al. | |
| 4,735,622 A * | 4/1988 | Acuff et al. | 604/361 |
| 4,743,238 A | 5/1988 | Colon et al. | |
| 4,776,800 A | 10/1988 | Anderson | |
| 4,810,562 A | 3/1989 | Okawa et al. | |
| 4,812,053 A | 3/1989 | Bhattacharjee | |
| 4,834,733 A | 5/1989 | Huntoon et al. | |
| 4,895,567 A | 1/1990 | Colon et al. | |
| 4,903,254 A | 2/1990 | Haas | |
| 4,909,879 A | 3/1990 | Ball | |
| 4,931,051 A * | 6/1990 | Castello | 604/361 |
| 4,940,464 A | 7/1990 | Van Gompel et al. | |
| 4,987,849 A * | 1/1991 | Sherman | 116/206 |
| 5,035,691 A | 7/1991 | Zimmel et al. | |
| 5,045,283 A | 9/1991 | Patel | |
| 5,046,272 A | 9/1991 | Vogt et al. | |
| 5,053,339 A | 10/1991 | Patel | |
| 5,058,088 A | 10/1991 | Haas et al. | |
| 5,066,711 A | 11/1991 | Colon et al. | |
| 5,078,708 A | 1/1992 | Haque | |
| D323,920 S | 2/1992 | Pitts | |
| 5,089,548 A | 2/1992 | Zimmel et al. | |
| 5,104,116 A | 4/1992 | Pohjola | |
| 5,130,290 A | 7/1992 | Tanimoto | |
| 5,133,087 A | 7/1992 | Machida et al. | |
| 5,167,652 A | 12/1992 | Mueller | |
| 5,197,958 A | 3/1993 | Howell | |
| 5,224,405 A | 7/1993 | Pohjola | |
| 5,226,992 A | 7/1993 | Morman | |
| 5,286,543 A | 2/1994 | Ungpiyakul et al. | |
| 5,354,289 A | 10/1994 | Mitchell et al. | |
| H1376 H | 11/1994 | Osborn, III et al. | |
| 5,364,132 A | 11/1994 | Haas et al. | |
| 5,389,093 A | 2/1995 | Howell | |
| 5,411,295 A | 5/1995 | Bates et al. | |
| 5,435,010 A | 7/1995 | May | |
| 5,458,590 A | 10/1995 | Schleinz et al. | |
| 5,578,023 A * | 11/1996 | Schneider | 604/332 |
| 5,683,752 A | 11/1997 | Popp et al. | |
| 5,766,212 A | 6/1998 | Jitoe et al. | |
| 5,766,389 A * | 6/1998 | Brandon et al. | 156/64 |
| 5,897,541 A | 4/1999 | Uitenbroek et al. | |
| 5,897,546 A | 4/1999 | Kido et al. | |
| 6,045,543 A | 4/2000 | Pozniak et al. | |
| 6,075,178 A * | 6/2000 | La Wilhelm et al. | 604/361 |
| 6,198,018 B1 * | 3/2001 | Curro | 604/367 |
| 6,238,519 B1 | 5/2001 | Jones et al. | |
| 6,297,424 B1 * | 10/2001 | Olson et al. | 604/361 |
| 6,307,119 B1 * | 10/2001 | Cammarota et al. | 604/361 |

\* cited by examiner

ABSORBENT ARTICLES HAVING WETNESS INDICATING GRAPHICS AND EMPLOYING MASKING TECHNIQUES

BACKGROUND OF THE INVENTION

The present invention relates to absorbent articles, and more particularly to absorbent articles having a wetness indicator.

Various types of moisture or wetness indicators have been suggested for use in absorbent articles. Certain of these wetness indicators have been formed of compositions that are liquid soluble or liquid dispersible. These liquid soluble indicators rely on the dispersion of the composition upon contact with liquid to signal that liquid is present.

One difficulty associated with present absorbent articles containing a liquid soluble wetness indicator is that the wetness indicator composition may not disperse sufficiently. In particular disposable absorbent articles, for example, the wetness indicator composition can be placed on the interior surface of a moisture barrier so that the composition is visible through the moisture barrier prior to activation. Upon contact with liquid, the composition should disperse sufficiently so that the wetness indicator composition is no longer visible through the moisture barrier. Unfortunately, however, the liquid soluble wetness indicator compositions in present absorbent articles do not disperse thoroughly or rapidly enough to be completely invisible through the moisture barrier. A portion of the composition can remain visible, making the wetness indicator appear smudged. Not only is this undesirable from an aesthetic perspective, but it can also create confusion as to whether the indicator is signaling the presence of liquid in the absorbent article.

SUMMARY OF THE INVENTION

In response to the discussed deficiencies associated with prior absorbent articles, an absorbent article incorporating a liquid soluble wetness indicator has been developed that minimizes the likelihood of smudges appearing after activation. Various masking techniques can be used in combination with the wetness indicating graphic to lessen the degree to which the wetness indicator composition is able to be seen through the outer cover after contact with liquid.

Hence, in one embodiment, the invention concerns an absorbent article that includes an outer cover having in interior surface and an opposite exterior surface, and an absorbent assembly disposed on the interior surface of the outer cover. The absorbent article also includes a liquid soluble fading graphic that is disposed on the outer cover and in liquid communication with the absorbent assembly, and a masking graphic that is disposed on the outer cover and at least partially peripherally surrounding the fading graphic.

In another embodiment, the invention concerns an absorbent article that includes an outer cover having in interior surface and an opposite exterior surface, and an absorbent assembly disposed on the interior surface. A liquid soluble fading graphic is disposed on the outer cover and in liquid communication with the absorbent assembly, and a liquid soluble masking graphic is disposed on the outer cover and superposed on the fading graphic.

In a further embodiment, the invention concerns an absorbent article that includes an outer cover having in interior surface and an opposite exterior surface, and an absorbent assembly disposed on the interior surface. A first graphic formed of a liquid soluble composition is disposed on the outer cover and in liquid communication with the absorbent assembly. A second graphic formed of a liquid soluble composition is also disposed on the outer cover. The absorbent article further includes a permanent masking graphic that is disposed on the outer cover at least partially peripherally surrounding the first graphic and superposed on the second graphic. In particular embodiments, the absorbent article can also include a liquid soluble masking graphic superposed on the first graphic.

The term "fading graphic" is used herein to refer to a graphic that becomes invisible or becomes significantly less visible when exposed to urine. Suitable fading graphics comprise compositions such as inks that are soluble in aqueous solutions such as urine. The wetness indicating composition is positioned in the absorbent article so that it becomes wet and dissolves when the product is insulted with liquid. Once dissolved, the wetness indicating composition washes away from the outer cover and is obscured by the outer cover. As a result, the fading graphic seems to disappear from view.

Suitable urine-soluble inks are available from a variety of commercial vendors, such as Sun Chemical Corp. of Philadelphia, Pa. USA under the trade designation AQUA DESTRUCT. Particular urine-soluble compositions are disclosed in U.S. Pat. No. 4,022,211 issued May 10, 1977 to Timmons et al., which is incorporated herein by reference. The ink color can be selected to provide a pleasing appearance and graphic impact, including fading rapidly upon contact with liquid. To facilitate rapid fading, the fading graphics can comprise line drawings having a line width of from about 1 to about 2 millimeters.

The absorbent article can also include on or more permanent graphics, which for diapers and training pants may provide the caregiver with a greater opportunity to interact with the child. The term "permanent graphic" is used herein to refer to a graphic that does not substantially change its degree of visibility when the absorbent article is insulted with urine, in simulated use conditions. The change in visibility of a graphic or a portion of a graphic can be determined based on a person's observation of the graphic before and after the article containing the graphic is exposed to liquid. For purposes hereof, an article is exposed to liquid by immersing the article completely in an aqueous solution containing 0.9 weight percent sodium chloride, used at room temperature ($\cong 23°C$.), for a period of twenty minutes. After 20 minutes the product is removed from the aqueous solution and placed on a TEFLON™ coated fiberglass screen having 0.25 inch openings, which is commercially available from Taconic Plastics Inc., Petersberg, N.Y., USA, which in turn is placed on a vacuum box and covered with a flexible rubber dam material. A vacuum of 3.5 kilopascals (0.5 pounds per square inch) is drawn in the vacuum box for a period of 5 minutes, after which the article is removed and observed. The person with normal or corrected vision of about 20–20 should make the observations from a distance of 1 meter in an environment providing 30 footcandles (320 Lux) of illumination. Changes: in the visibility of the graphic should be identified, and distinguished where necessary from changes in the color of other materials such as fluff pulp within an absorbent assembly. Desirably, the permanent graphic can be configured so that the entire graphic also does not substantially change its appearance, size or shape when the product is insulted with liquid or exposed to the environment.

The term "masking graphic" is used herein to mean a graphic adapted to obscure the visibility of a fading graphic after the fading graphic comes into contact with a liquid. The masking graphic can in particular embodiments, comprise a permanent graphic, comprise a graphic that is liquid soluble, or comprise both a permanent graphic and a graphic that is liquid soluble. The general term "graphic" is used herein to mean: any design, pattern, or the like that is or becomes visible on an absorbent article, and specifically includes text messages that consist of one or more alphanumeric symbols, pictorial images that consist of one or more pictures, and combinations thereof; and, in relation to a masking graphic, any design, pattern, or the like that is disposed on a substrate with the result of obscuring the visibility of an associated graphic after contact with liquid.

The masking graphic is suitably formed with a color that matches colors of surrounding materials or permanent graphics of the absorbent article. For example, the masking graphic can be substantially the same color as the outer cover, substantially the same color as the absorbent assembly, or the like. In one particular embodiment, the masking graphic is white in color, which may be particularly advantageous because the outer cover and absorbent assembly in many commercially available disposable absorbent articles are white.

In use, the active graphic can appear or fade when an accident occurs and urine comes into contact with the active graphic. Desirably, the active graphic appears or fades in about 3 minutes or less, particularly in about 1 minute or less, and more desirably in about 20 seconds or less, when the absorbent article is insulted with 200 milliliters or more of urine, and, more desirably about 40 to about 60 milliliters or more of urine.

Permanent graphics can be positioned anywhere on the outer cover, and in particular embodiments can desirably be positioned in the front waist region along or near the longitudinal centerline of the product. Particular arrangements for permanent and wetness indicating graphics are disclosed in U.S. patent application Ser. No. 09/333,223, filed on Jun. 15, 1999 by Cammarota et al. and titled "Absorbent Articles Having Wetness Indicating Graphics Incorporating A Training Zone," now U.S. Pat. No. 6,307,119 B1 granted Oct. 23, 2001, and U.S. patent application Ser. No. 09/333,222, filed on Jun. 15, 1999 by Olson et al. and titled "Absorbent Articles Having Wetness Indicating Graphics Providing An Interactive Training Aid," now U.S. Pat. No. 6,297,424 B1 granted Oct. 2, 2001.

The fading graphics can but need not necessarily be positioned closer to the transverse centerline of the product than the permanent graphics. In particular embodiments, the fading graphics are positioned between the transverse centerline of the product and the permanent graphic so as to be properly focussed and not hidden from view during use. Locating the fading graphics in the crotch region of the product, near the target spot for urination, can also assist with rapid exposure of the fading graphic to urine upon insult. It is desirable to locate fading graphics on the area of the outer cover that is most likely to experience wetness during the first void. Of course, alternative positioning of the permanent and fading graphics are possible, such as the permanent graphic in the crotch region and the fading graphic in one of the waist regions, both permanent and fading graphics in one or both of the waist regions and/or the crotch region, or the like. The fading graphics can but need not necessarily be positioned on one or more sides of the permanent graphics, such as "floating" under the permanent graphic. Alternatively, the permanent graphic can surround the fading graphic and vice versa.

In one particular embodiment, all of the fading graphics are located in a distinct active graphic region where the child can focus attention. The active graphic region suitably has a length dimension measured parallel to the longitudinal centerline of about 10 centimeters, more particularly about 9 centimeters, and a width dimension measured parallel to the transverse centerline of about 6 centimeters. The active graphic region can, for instance, be spaced from the first end edge of the product by approximately 13 to 16 centimeters.

There can be one or more fading graphics. It is believed desirable to use a plurality of fading graphics in order provide the greatest impact to the caregiver and/or child. In particular embodiments, a training pant comprises 3 or more fading graphics, particularly from 4 to 8, such as 5 arranged in a 2-1-2 pattern.

The size of the fading graphics may depend in part on their number and type. It is generally preferred that the fading graphics have a size of at least about 1.5 by 1.5 centimeter and less than about 3 by 3 centimeters, and particularly at least about 1.8 by 1.8 centimeter and less than about 2.5 by 2.5 centimeters.

The overall size of the permanent graphic can be significantly larger than the overall size of each discrete fading graphic. In particular embodiments, for instance, the permanent graphic has a size measured by overall surface area that is at least twice as large, and more particularly at least three times as large, as the size of a single fading graphic. The maximum length dimension of the permanent graphic, measured parallel to the longitudinal centerline, is desirably about 8 to about 9 centimeters.

The permanent and fading graphics are suitably disposed on the outer cover. The term "disposed on" and variations thereof are intended to mean that one element can be integral with another element, or that one element can be a separate structure bonded to or placed with or placed near another element. Thus, the graphics can be formed or applied directly or indirectly to a surface of the outer cover, formed or applied between layers of a multiple layer outer cover, formed or applied to a substrate that is placed with or near the outer cover, formed or applied within a layer of the outer cover or another substrate, or other variations or combinations thereof. In particular embodiments, the graphics can be printed, sprayed, or otherwise applied directly on a layer of the outer cover. In other embodiments, the graphics can be applied to a layer placed with or near the outer cover, such as a substrate associated with the absorbent assembly, including but not limited to tissue layers, liquid handling layers, absorbent layers, or the like.

The permanent graphics can be located on, the exterior surface of the outer cover to enhance the visual impact of the permanent graphics. Alternatively, however, the permanent graphics can be located on the interior surface of the outer cover or between layers of a multilayer outer cover, provided the permanent graphics remain visible from the exterior of the Product.

The fading graphics can be located on the interior surface of the outer cover, which is particularly desirable for graphics that are triggered by urine in order to enhance the speed at which the graphics are contacted with urine and thus change their visual appearance. The outer cover desirably comprises a material that is formed or treated to be liquid impermeable. In alternative embodiments, the outer cover can comprise a material that is formed or treated to be at least partially liquid permeable. In this latter case, the fading graphics can be located between layers of a multilayer outer cover. Regardless of location, fading graphics should be visible from the exterior of the product before activation.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, can spread or be transported parallel to the plane of, the liquid impermeable layer or laminate, but this is not considered to be within the meaning of "liquid impermeable" when used herein.

The outer cover can comprise a transparent or translucent material. Desirably the outer cover has sufficient opacity or is treated according to the methods disclosed herein to mask a urine soluble ink after it has dissolved. Such an outer cover should not be so opaque that the graphics printed on the interior surface of the outer cover or adjacent to the interior surface are obscured. Polymer films used to form the outer cover can be treated with titanium dioxide to make the film appear white and to develop sufficient opacity to mask urine, BM and dissolved inks. Examples of suitable outer cover materials include films formed of polyethylene, polypropylene, cataloy, bi-component, any polymer based extruded film, or the like. One such film is a polyethylene film having a thickness of about 0.02 millimeter (0.75 mil).

The permanent and fading graphics can be formed on or applied to the outer cover or another substrate bonded to or placed with or placed near the outer cover by any suitable technique. The graphics are desirably registered with other components of the absorbent article during manufacture such that the graphics are positioned in the desired regions of the product.

The fading graphics are suitably in liquid communication with the absorbent assembly of the product. As used herein, the term "liquid communication" means that liquid such as urine is able to travel from one layer or element to another layer or element. The absorbent assembly can but need not include a slot or densified region, incorporate a liquid distribution layer, or the like, to channel or direct liquid to the location near the outer cover where the fading graphics are located.

It is theorized that migration of the dissolved wetness indicator composition away from the outer cover and into the absorbent assembly can improve the fading or disappearing quality of the graphics. To enhance this effect, the outer cover can be attached to the absorbent assembly in a windowpane design, whereby the fading graphic region of the outer cover is not bonded to the absorbent assembly and the regions of the outer cover surrounding the fading graphic region are bonded to the absorbent assembly. One suitable method and apparatus for adhesively bonding the outer cover to the absorbent assembly in a windowpane design is disclosed in U.S. Pat. No. 5,683,752 issued Nov. 4, 1997 to Popp et al., which is incorporated herein by reference.

Hence, in another embodiment, the invention concerns an absorbent article including an outer cover having in interior surface and an opposite exterior surface, and an absorbent assembly disposed on the interior surface. The absorbent article also includes a liquid soluble fading graphic that is disposed on the outer cover and in liquid communication with the absorbent assembly. The fading graphic is disposed in a fading graphic region and the absorbent assembly is bonded to the outer cover in regions other than the fading graphic region.

Absorbent articles suitable for use with the present invention include diapers, training pants, incontinence products, diaper pants, disposable underwear, medical garments, bandages, absorbent swimwear, wipes, or the like. Suitable training pants and diaper pants can have seamed side portions or refastenable side portions. The present invention is particularly suited for use with training pants or diaper pants to aid in toilet training. One particular training pant suitable for use with the present invention is disclosed in U.S. Pat. No. 4,940,464 issued Jul. 10, 1990 to Van Gompel et al., which is incorporated herein by reference. The van Gompel et al. patent describes various materials of which the training pant can be made, and a method of constructing a training pant. The training pant can also be constructed using the methods and apparatus disclosed in U.S. Pat. No. 5,766,389 issued Jun. 16, 1998 to Brandon et al., which is also incorporated herein by reference.

The above-mentioned and other features and advantages of the present invention and the manner of attaining them will become more apparent, and the invention itself will be better understood by reference to the drawings and the following description of the drawings.

DETAILED DESCRIPTION OF THE DRAWINGS

The principles of the present invention can be incorporated into a variety of absorbent articles, and particularly disposable absorbent articles. The term "disposable" refers to articles which are designed to be discarded after a limited use rather than being laundered or otherwise restored for reuse. For ease of explanation, the description hereafter will be in terms of a child's training pant.

Figure 1:
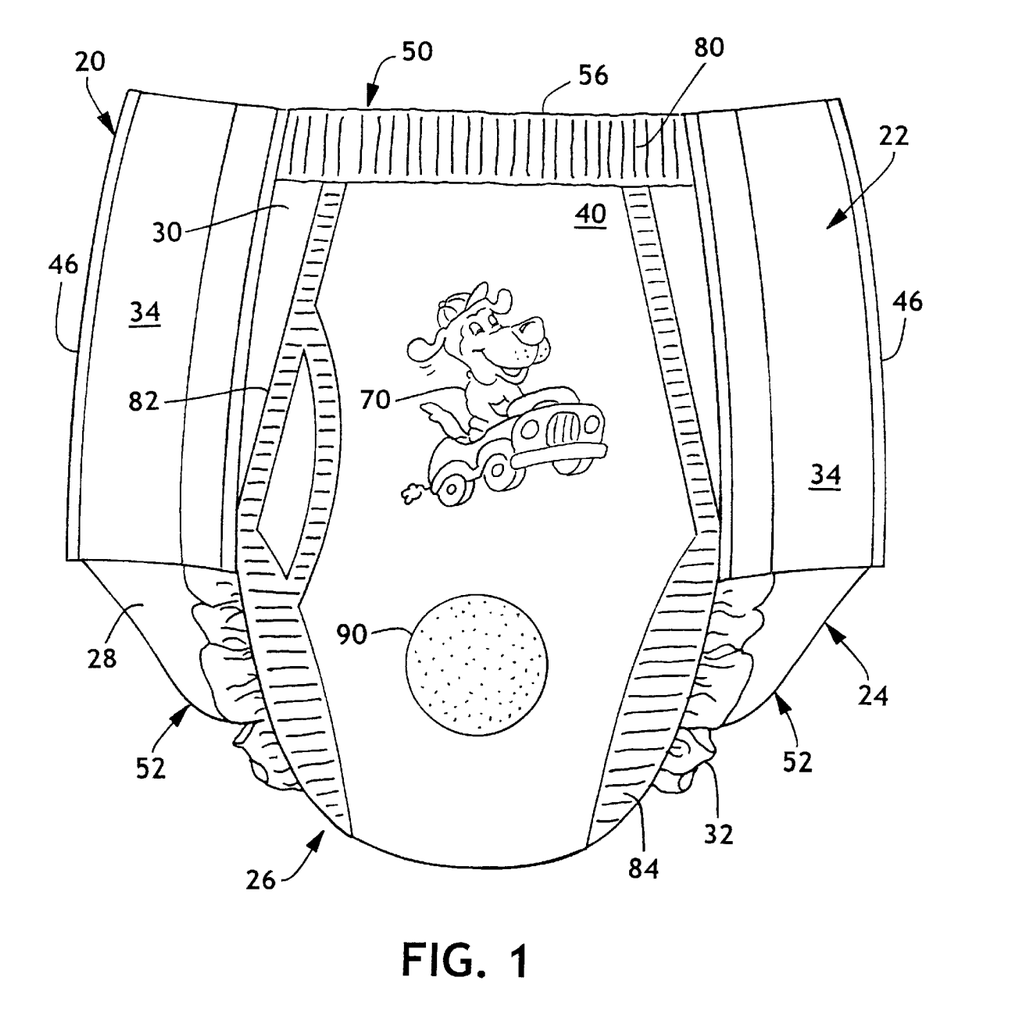
FIG. 1 illustrates a front perspective view of a training pant incorporating the principles of the present invention, showing both permanent graphics and fading graphics.
Figure 2:
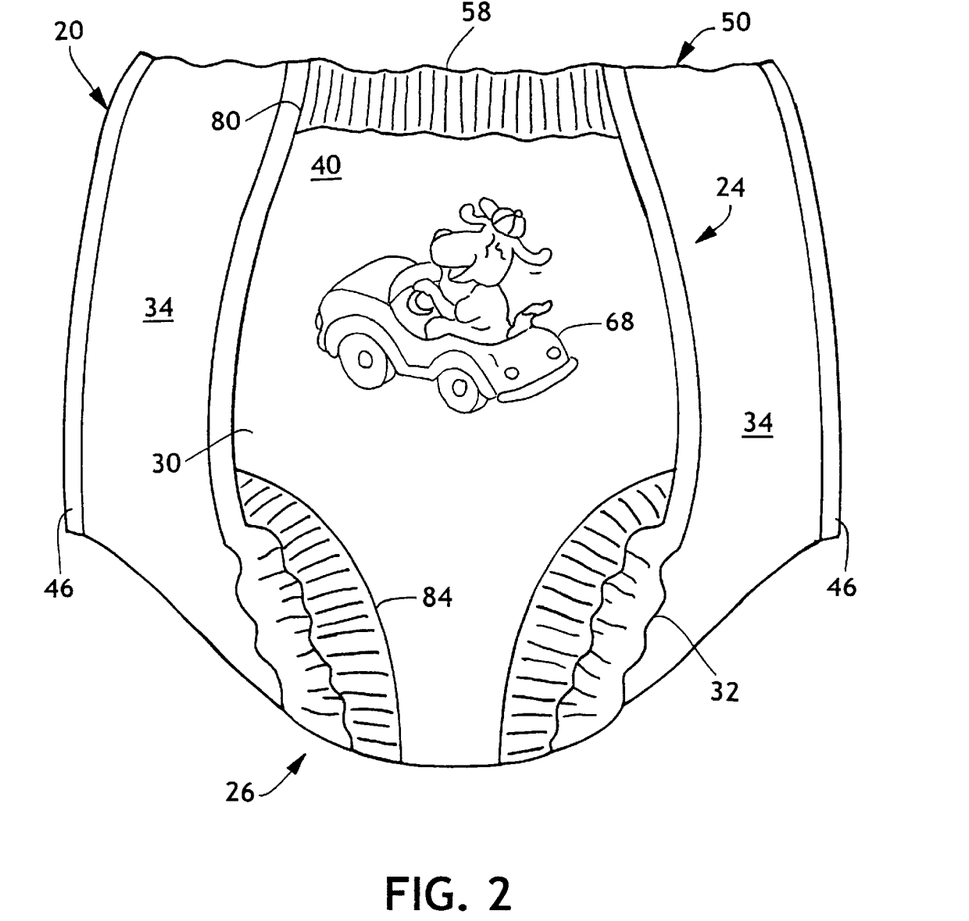
FIG. 2 illustrates a rear perspective view of the training pant of FIG. 1.
Figure 3:
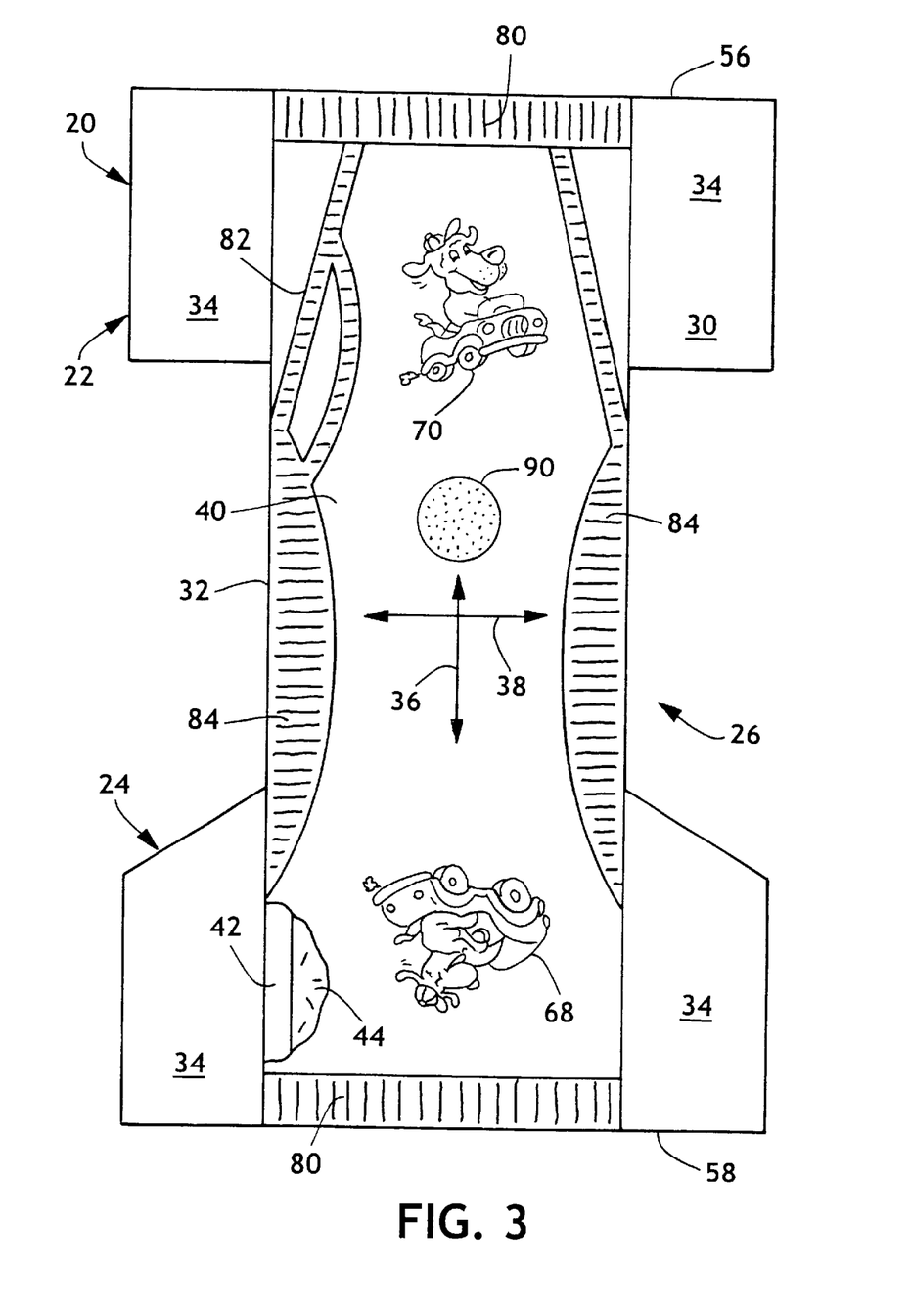
FIG. 3 illustrates a top plan, partially disassembled view of the training pant of FIGS. 1 and 2, in a stretched and laid flat condition and with portions broken away for purposes of illustration.

A training pant 20 is illustrated in a fully assembled condition in FIGS. 1 and 2 and in a partially disassembled, stretched and laid flat condition in FIG. 3. The training pant 20 defines a first or front waist region 22, a second or back waist region 24, a crotch region 26 positioned between and interconnecting the front and back waist regions, an inner surface 28 (FIG. 1) which is configured to contact the wearer, and an outer surface 30 opposite the inner surface which is configured to contact the wearer's clothing. The illustrated training pant 20 comprises an absorbent chassis 32 and a plurality of transversely opposed side panels 34. The absorbent chassis 32 and side panels 34 can be integrally formed or comprise two or more separate elements, as shown.

The training pant 20 defines a longitudinal centerline 36 (FIG. 3), a transverse centerline 38 (FIG. 3), a first or front longitudinal end edge 56, and a second or back longitudinal end edge 58. The first waist region 22 abuts the first longitudinal end edge 56, and the second waist region 24 abuts the second longitudinal end edge 58. "Longitudinal" and "transverse" have their customary meaning. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

The illustrated absorbent chassis 32 comprises an outer cover 40 and a bodyside liner 42 (FIG. 3) which is connected to the outer cover in a superposed relation. The absorbent chassis 32 also comprises an absorbent assembly 44 (FIG. 3) which is located between the outer cover and the bodyside liner, and can optionally include a pair of containment flaps (not shown).

With the training pant 20 in a fully assembled condition as illustrated in FIGS. 1 and 2, the front and back waist regions 22 and 24 are joined together by side seams 46 to define a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The side panels 34 comprise the portions of the training pant 20 which, when worn, are positioned on the side hip regions of the wearer. The longitudinal end edges 56 and 58 of the training pant 20 are configured to encircle the waist of the wearer when worn and provide the waist opening 50.

The absorbent chassis 32 is configured to contain and/or absorb any body exudates discharged from the wearer. For example, the absorbent chassis 32 desirably although not necessarily comprises the pair of containment flaps (not shown) which can be configured to provide a barrier to the transverse flow of body exudates. Suitable constructions and arrangements for the containment flaps are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 can include a front waist elastic, member, a rear waist elastic member, and leg elastic members (not shown), as are known to those skilled in the art. Waist elastic members and leg elastic members can be operatively joined to the outer cover 40 and/or bodyside liner 42 of the training pant 20. Elastic members for the containment flaps, waist elastics and leg elastics can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the leg elastic members comprise a plurality of dry-spun coalesced multifilament spandex elastomeric threads sold under the trade name LYCRA® and available from E. I. Du Pont de Nemours and Company, Wilmington, Del.

The outer cover 40 has an exterior surface corresponding to the outer surface 30 of the training pant and an opposite, interior surface. The outer cover 40 desirably comprises a material that is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis., or from National Starch and Chemical Company, Bridgewater, N.J. The liquid permeable outer layer can be any suitable material and desirably one that provides a generally cloth-like texture. One example of such a material is a 20 gsm (grams per square meter) spunbond polypropylene nonwoven web. The outer layer can also be made of those materials of which liquid permeable bodyside liner 42 is made. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials can also be used. The inner layer, or the liquid impermeable outer cover 40 when a single layer, prevents waste material from wetting articles, such as bedsheets and clothing, as well as the wearer and caregiver. A suitable liquid impermeable film for use as liquid impermeable inner layer, or a single layer liquid impermeable outer cover 40, is a 0.02 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

As shown in FIGS. 1–3, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" fore boys, ruffles for girls; highlighting areas of the product to change the appearance of the size of the product; registering wetness indicators, temperature indicators, and the like in the product; registering a back label, or a front label, in the product; and registering written instructions at a desired location in the product The illustrated training pant 20, which is designed for use by young boys, includes registered outer cover graphics, including interactive wetness indicating graphics. More specifically, the training pant includes a permanent graphic 70 comprising a dog with human-like expressions and wearing a shirt and a hat and a driving an automobile. The training pant also includes a fading graphic 90 comprising a circular picture, for example a circle formed of a composition having a color different than the color of the outer cover 40. The outer cover graphics also include a simulated elastic waistband 80, a simulated fly opening 82, and simulated elastic leg bands 84, all of which can be permanent graphics. A supplemental graphic 68 (FIG. 2) can be included in the back waist region 24, and as illustrated comprises a reversed image of the dog in the automobile. The dog, automobile and circle are shown for purposes of illustration, however, the graphics of the absorbent article can take any form that is suitable for the intended use of the absorbent article.

The fading graphic 90 can be disposed on the interior surface of the outer cover 40 and be visible from the exterior surface of the outer cover. The fading graphic 90 is in liquid communication with the absorbent assembly 44, meaning that liquid such as urine is capable of moving between the fading graphic 90 and the absorbent assembly under ordinary use conditions. When the child wets the training pant 20, liquid is communicated to the fading graphic 90 whereupon the fading graphic dissolves so that it is no longer visible from the exterior of the product.

Figure 4:
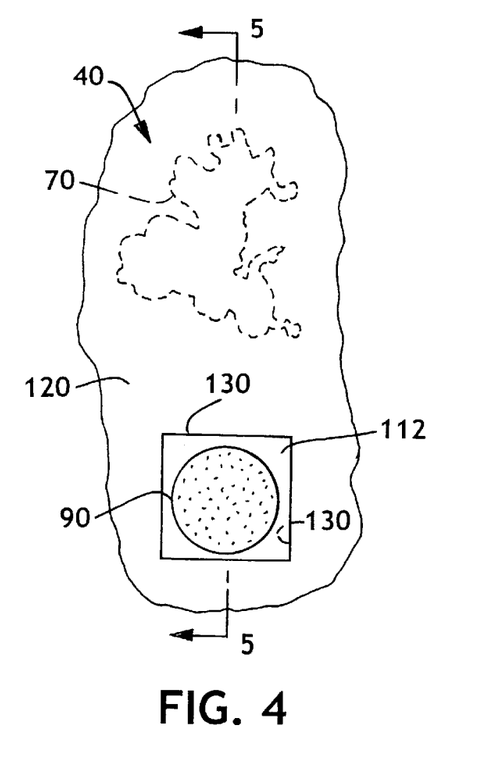
FIG. 4 representatively shows a top plan view of a portion of an outer cover of the training pant of FIGS. 1 and 2, viewed from an inner surface.
Figure 5:
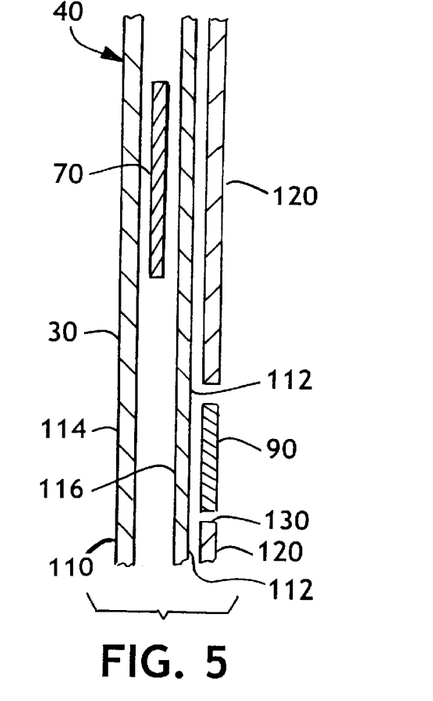
FIG. 5 illustrates an exploded section view of the outer cover taken from the plane of the line 5—5 in FIG. 4, with the various components shown enlarged from actual size for purposes of illustration.

A portion of the outer cover 40 is shown separately in FIGS. 4 and 5. The outer cover 40 has an exterior surface 110 and an opposite interior surface 112, where the plan view of FIG. 4 is from the perspective of the interior surface. The illustrated outer cover 40 consists of a two-layer composite comprising an outer layer 114 and an inner layer 116. The outer and inner layers can be bonded together by adhesives, thermal bonds, ultrasonic bonds, or other suitable means.

The permanent and fading graphics can be disposed on the outer cover 40, which includes, in particular, on the exterior surface 110, on the interior surface 112, between the outer and inner layers 114 and 116, on either or both facing surfaces of the outer and inner layers 114 and 116, on the surface of the absorbent assembly 44 that faces the outer cover, or between the absorbent assembly and the outer cover. The inner layer 116 of the outer cover 40 is desirably formed of a material that is liquid impermeable, in which case the fading graphic 90 is disposed on the interior surface 112 of the outer cover 40, as illustrated, on the surface of the absorbent assembly 44 that faces the outer cover, or between the absorbent assembly and the outer cover. The permanent and active graphics need not be located in the same position or on the same substrate. In the illustrated embodiment, the permanent graphic 70 is positioned between the outer and inner layers 114 and 116 of the outer cover 40.

In the embodiment of FIGS. 4 and 5, a masking graphic 120 is disposed on the outer cover 40, and in particular is disposed in the interior surface 112 of the outer cover. Alternatively, the masking graphic 120 can be positioned between the layers 114 and 116 of the outer cover or on the exterior surface 110 of the outer cover.

The illustrated masking graphic 120 desirably at least partially peripherally surrounds the fading graphic 90, and can, as illustrated, completely encircle the fading graphic. Beneficially, the masking graphic 120 can be placed in close proximity to the fading graphic 90. In particular, the masking graphic 120 defines an edge 130 (FIG. 4) that is disposed toward the fading graphic 90, and the edge 130 of the masking graphic 120 is positioned within about 1 centimeter of the fading graphic, particularly within about 0.5 centimeter of the fading graphic, and more particularly within about 0.2 centimeter of the fading graphic, for improved performance. The edge 130 of the masking graphic is desirably located in such close proximity to the fading graphic 90 on at least two sides of the fading graphic, particularly on at least three sides of the fading graphic, and more particularly on all four sides of the fading graphic. The sides of a fading graphic in this regard are considered to be the four points at which the perimeter of the fading graphic intersect two perpendicular axes which are transposed on the fading graphic, where the axes do not necessarily correspond with the longitudinal and transverse axes 36 and 38 of the absorbent article. As shown in FIG. 4, however, the masking graphic 120 is desirably but not necessarily isolated peripherally from the fading graphic 90, meaning that the edge of the masking graphic at most abuts the fading graphic but does not overlap the fading ;graphic, so that the masking graphic is not superposed on the fading graphic.

In addition to being located in close proximity to the fading graphic 90, the masking graphic 120 desirably possesses sufficient surface area to enhance masking. For a permanent masking graphic, for example, the masking graphic 120 is desirably sufficiently large so that the dissolved fading graphic 90 is disposed behind the permanent masking graphic and shielded from view. Alternatively for a liquid soluble masking graphic, the masking graphic 120 is desirably sufficiently large so that the dissolved fading graphic 90 is adequately mixed with the dissolved masking graphic and thereby obscured from view. Thus, in particular embodiments, the masking graphic 120 comprises a substantially continuous graphic extending from the edge 130 of the masking graphic that is located in proximity to the fading graphic 90 for a distance, of about 1 centimeter or more, particularly about 2 centimeters or more, and more particularly about 3 centimeters or more, for improved masking of the dissolved fading graphic. The term "substantially continuous" as used herein in relation to a masking graphic means that the masking graphic is generally solid and lacks sufficient void areas to permit unobstructed observation of dissolved fading graphic composition through the masking agent. The masking graphic 120 desirably extends substantially continuously from the edge 130 for the above-stated distances on at least two sides, particularly on at least three sides, and more particular on all four sides, of the fading graphic 90.

The masking graphic 120 can comprise a permanent graphic so that dissolved portions of the fading graphic 90 are hidden behind the masking graphic. Alternatively, the masking graphic 120 can be liquid soluble so that the dissolved fading graphic 90 and the dissolved masking graphic 120 mix together to obscure visual detection of the fading graphic. Particularly in this latter case, the masking graphic 120 can comprise an optical brightener, in order to increase the intensity of the masking component and enhance the disappearing effect. Alternatively, a separate layer of optical brightener can be disposed on the outer cover and superposed on the fading graphic or on the masking graphic. Suitable optical brighteners include, for example, UVITEX OB manufactured by Ciba-Geigy, and LEU-COPURE EGM manufactured by Sandoz Chemicals Corporation.

Figure 6:
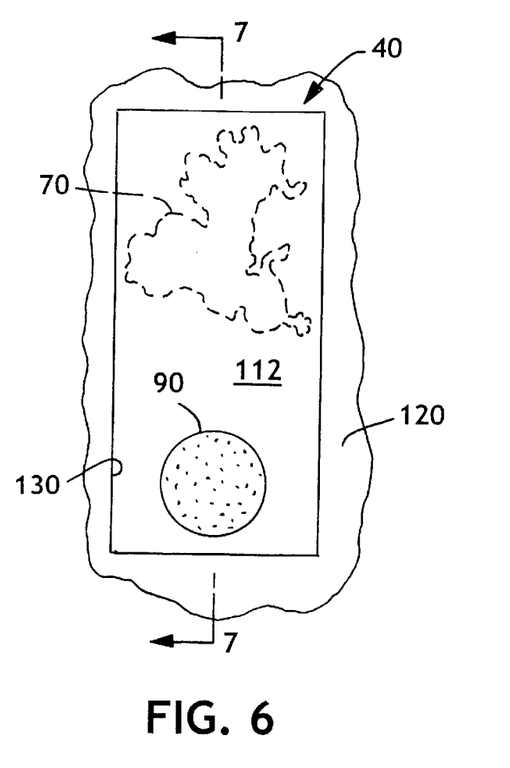
FIG. 6 representatively shows a top plan view similar to FIG. 4 but showing a portion of an alternative outer cover.
Figure 7:
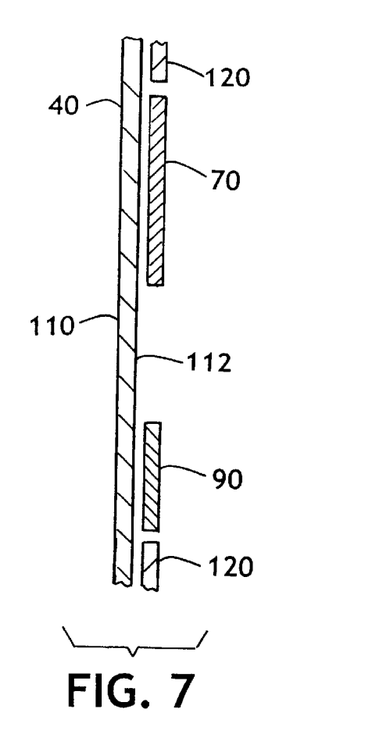
FIGS. 7 illustrates an exploded section view of the outer cover taken from the plane of the line 7—7 in FIG. 6, with the various components shown enlarged from actual size.

An alternative configuration of the outer cover 40 and graphics is illustrated in FIGS. 6 and 7. In this embodiment, the outer cover 40 consists of a single layer having an exterior surface 110 and an opposite interior surface 112. The permanent graphic 70 and the fading graphic 90 are both disposed on the interior surface 112 of the outer cover 40. The masking graphic 120 partially peripherally surrounds both the fading graphic 90 and the permanent graphic 70, although as illustrated the edge of the masking graphic is located in particularly close proximity to the fading graphic on only three sides. The masking graphic 120 is also isolated peripherally from the fading graphic 90. The masking graphic 120 can comprise either a permanent graphic or a graphic that is liquid soluble.

Figure 8:
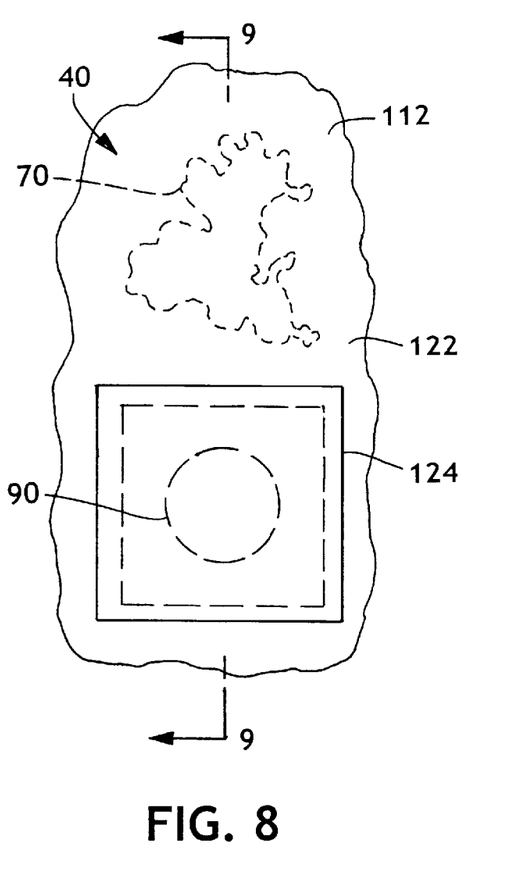
FIG. 8 representatively shows a top plan view similar to FIGS. 4 and 6 but showing a portion of another alternative outer cover.
Figure 9:
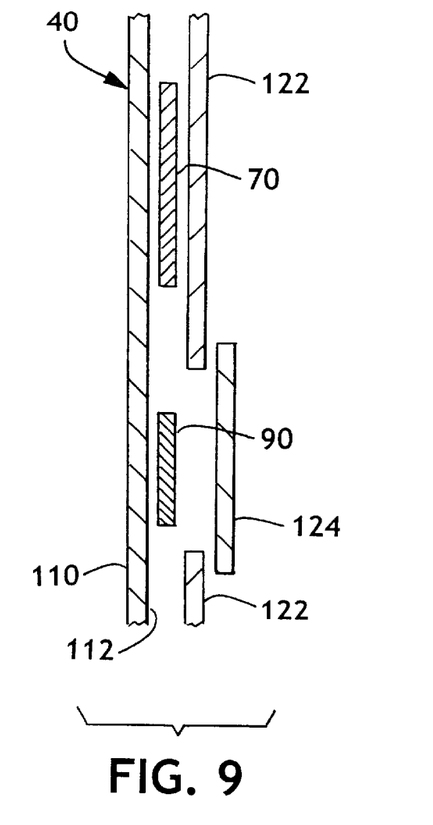
FIG. 9 illustrates an exploded section view of the outer cover taken from the plane of the line 9—9 in FIG. 8, with the various components shown enlarged from actual size.

Another alternative configuration of the outer cover 40 and graphics is illustrated in FIGS. 8 and 9. The illustrated the outer cover 40 consists of a single layer having an exterior surface 110 and an opposite interior surface 112, and both the permanent graphic 70 and the fading graphic 90 are both disposed on the interior surface 112 of the outer cover 40.

As depicted, the masking graphic consists of a first masking graphic 122 and a second masking graphic 124. The first masking graphic 122 is disposed on the outer cover 40 and peripherally surrounds the fading graphic 90. The second masking graphic 124 is disposed on the outer cover and is superposed on the fading graphic 90. The second masking graphic 124 is suitably formed of a liquid soluble material so that the dissolved fading graphic 90 and the dissolved second masking graphic mix together to obscure visual detection of the fading graphic.

The first masking graphic 122 can comprise a permanent graphic so that dissolved portions of the fading graphic 90 are hidden behind the first masking graphic. In this case, the permanent graphic 70 can be formed of a liquid soluble composition because it is overprinted with the, permanent masking graphic. This can be advantageous for certain printing configurations. The first masking graphic 122 can alternatively be formed of a liquid soluble material. In this latter case, both the dissolved first and second masking graphics 122 and 124 can mix with the dissolved fading graphic 90 upon liquid insult. The liquid permeable bodyside liner 42 generally overlies the outer cover 40 and absorbent assembly 44, and can but need not shave the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be compose ed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent assembly 44 (FIG. 3) is positioned between the outer cover 40 and the bodyside liner 42, which components can be joined together by any suitable means such as adhesives as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 can optionally be wrapped or encompassed by a suitable tissue wrap that maintains the integrity and/or shape of absorbent assembly.

Figure 10:
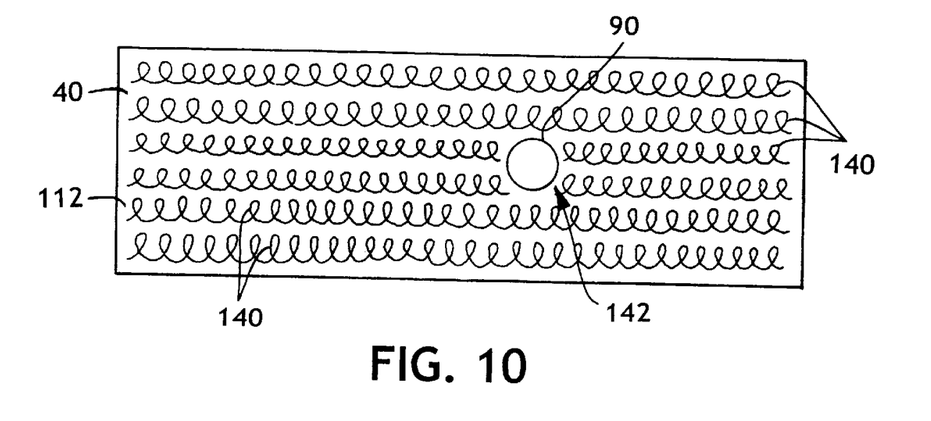
FIGS. 10 and 11 representatively show top plan views of a portion of an outer cover of further alternative absorbent articles according to the present invention, viewed from an inner surface.
Figure 11:
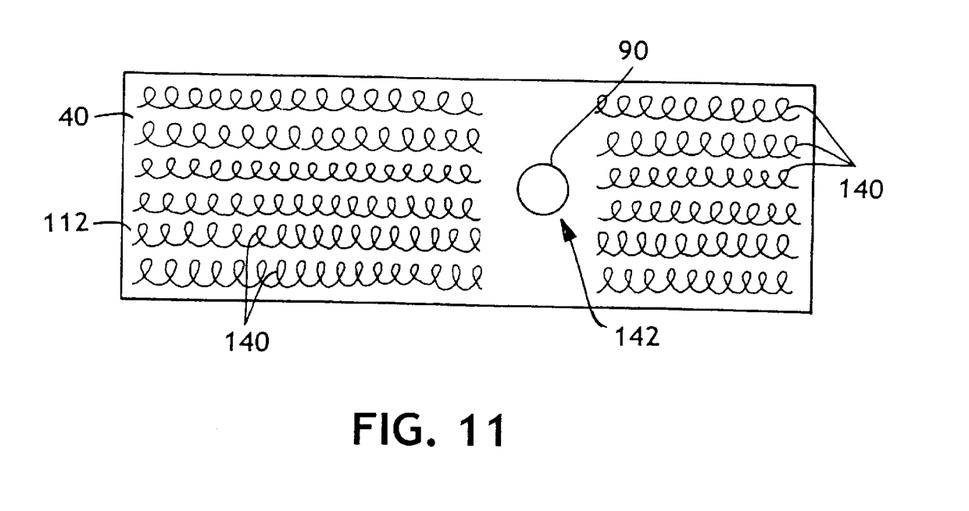

Another technique for masking the dissolved fading graphic composition is illustrated in FIGS. 10 and 11. A fading graphic 90 is shown on the interior surface 112 of an outer cover 40. The outer cover 40 can be bonded to the absorbent assembly 44 (not shown in FIG. 10) using an adhesive 140. The illustrated adhesive pattern comprises a plurality of swirls of adhesive, such as a hot melt adhesive, although other patterns of adhesive such as lines, stripes, spray patterns, meltblown patterns, printed patterns or the like are also suitable. The adhesive 140 can be applied to the outer cover 40 so that the region of the outer cover that includes the fading graphic 90, referred to as the fading graphic region 142, is not bonded to the absorbent assembly. It is theorized that this beneficially improves masking of the fading graphic composition in the following manner. When liquid is introduced into the absorbent article, the fading graphic composition will dissolve and enter the absorbent assembly. The spacing between the outer cover 40 and the absorbent assembly 44, which then contains the dissolved fading graphic composition, will improved masking of the fading graphic composition through the outer cover.

The adhesive 140 can completely surround or partially peripherally surround the fading graphic 90. For example, in FIG. 10, the regions of the outer cover 40 that substantially surround the fading graphic region 142 can bonded to the absorbent assembly. Moreover, a region that, peripherally surrounds the fading graphic 90, and particularly measuring about 1 centimeter or more, particularly about 2 centimeters or more, and more particularly about 3 centimeters or more outward from the fading graphic, can be void of adhesive 140 and therefore not bonded to the absorbent assembly, for improved performance. The adhesive 140 is depicted as partially peripherally surrounding the fading graphic 90 in FIG. 11.

The absorbent chassis 32 can also incorporate other materials that are designed primarily to receive, temporarily store, and/or transport liquid along the mutually facing surface with absorbent assembly 44, thereby maximizing the absorbent capacity of absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C. U.S.A.

As noted previously, the illustrated training pant 20 has a side panel 34 disposed on each side of the absorbent chassis 32. In the illustrated embodiment, the pair of transversely opposed side panels 34 are permanently bonded to the absorbent chassis 32 and permanently bonded to one another, using attachment means known to those skilled in the art such as adhesive, thermal or ultrasonic bonding.

The side panels 34 desirably comprise an elastic material capable of stretching in a direction parallel to the transverse axis 49 of the training pant 20. Suitable elastic materials, as well as one described process of incorporating elastic side panels into a training pant, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13,1993 to Mormon; and European Patent Application No. EP 0 217 032 published on Apr. 8, 1987 in the names of Taylor et al.; all of which are incorporated herein by reference. Alternatively, the side panel material can comprise other woven or nonwoven materials, such as those described above as being suitable for the outer cover 40 or bodyside liner 42.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An absorbent article comprising:
   an outer cover having an interior surface and an opposite exterior surface;
   an absorbent assembly disposed on the interior surface;
   a liquid soluble fading graphic disposed on the outer cover and in liquid communication with the absorbent assembly; and
   a masking graphic disposed on the outer cover at least partially peripherally surrounding the fading graphic, wherein the masking graphic is liquid soluble.

2. The absorbent article of claim 1, wherein the masking graphic is superposed on the fading graphic.

3. An absorbent article comprising:
   an outer cover having an interior surface and an opposite exterior surface;

an absorbent assembly disposed on the interior surface;
a liquid soluble fading graphic disposed on the outer cover and in liquid communication with the absorbent assembly; and
a masking graphic disposed on the outer cover at least partially peripherally surrounding the fading graphic, wherein the masking graphic is white.

4. An absorbent article comprising:
an outer cover having an interior surface and an opposite exterior surface;
an absorbent assembly disposed on the interior surface;
a liquid soluble fading graphic disposed on the outer cover and in liquid communication with the absorbent assembly; and
a masking graphic disposed on the outer cover at least partially peripherally surrounding the fading graphic, wherein the masking graphic and outer cover are substantially a same color.

5. An absorbent article comprising:
an outer cover having an interior surface and an opposite exterior surface;
an absorbent assembly disposed on the interior surface;
a liquid soluble fading graphic disposed on the outer cover and in liquid communication with the absorbent assembly; and
a masking graphic disposed on the outer cover at least partially peripherally surrounding the fading graphic, wherein the masking graphic and absorbent assembly are substantially a same color.

6. An absorbent article comprising:
an outer cover having an interior surface and an opposite exterior surface;
an absorbent assembly disposed on the interior surface;
a liquid soluble fading graphic disposed on the outer cover and in liquid communication with the absorbent assembly; and
a masking graphic disposed on the outer cover at least partially peripherally surrounding the fading graphic, the absorbent article further comprising a permanent graphic disposed on the outer cover.

7. Absorbent article of claim 6, wherein the masking graphic is superposed on the permanent graphic.

8. The absorbent article of claim 6, wherein the outer cover comprises a liquid permeable outer layer and a liquid impermeable inner layer, the fading graphic is disposed on one surface of the inner layer that forms the interior surface of the outer cover, and the permanent graphic is disposed on an opposite surface of the inner layer.

9. An absorbent article comprising
an outer cover having an interior surface and an opposite exterior surface;
an absorbent assembly disposed on the interior surface;
a liquid soluble fading graphic disposed on the outer cover and in liquid communication with the absorbent assembly; and
a masking graphic disposed on the outer cover at least partially peripherally surrounding the fading graphic, wherein the outer cover is adhesively attached to the absorbent assembly in a windowpane pattern, and the region of the outer cover containing the fading graphic is unadhered to the absorbent assembly.

10. An absorbent article comprising:
an outer cover having an interior surface and an opposite exterior surface;
an absorbent assembly disposed on the interior surface;
a liquid soluble fading graphic disposed on the out cover and in liquid communication with the absorbent assembly; and
a liquid soluble masking graphic disposed on the outer cover and superposed on the fading graphic.

11. The absorbent article of claim 10, wherein the masking graphic is white.

12. The absorbent article of claim 10, wherein the masking graphic and outer cover are substantially a same color.

13. The absorbent article of claim 10, wherein the masking graphic and absorbent assembly are substantially a same color.

14. The absorbent article of claim 10, wherein the masking graphic is formed with a color that matches a color of a surrounding material or permanent graphic.

15. The absorbent article of claim 10, wherein the masking graphic comprises an optical brightener.

16. The absorbent article of claim 10, further comprising an optical brightener disposed on the outer cover and superposed on the fading graphic.

17. The absorbent article of claim 10, further comprising a permanent graphic disposed on the outer cover.

18. The absorbent article of claim 17, further comprising a second masking graphic disposed on the outer cover and superposed on the permanent graphic, the second masking graphic being a permanent graphic.

19. The absorbent article of claim 17, wherein the outer cover comprises a liquid permeable outer layer and a liquid impermeable inner layer, the fading graphic is disposed on one surface of the inner layer that forms the Interior surface of the outer cover, and the permanent graphic is disposed on an opposite surface of the inner layer.

20. The absorbent article of claim 17, wherein the masking graphic is superposed on the permanent graphic.

21. The absorbent article of claim 18, wherein, the outer cover is adhesively attached to the absorbent assembly in a windowpane pattern, and the region of the outer cover containing the fading graphic is unadhered to the absorbent assembly.

22. An absorbent article comprising:
an outer cover having an interior surface and an opposite exterior surface;
an absorbent assembly disposed on the interior surface;
a first graphic disposed on the outer cover and in liquid communication with the absorbent assembly, the first graphic comprising a liquid soluble composition;
a permanent masking graphic disposed on the outer cover at least partially peripherally surrounding the first graphic;
and a second graphic disposed on the outer cover and comprising a liquid soluble composition, the second graphic being overprinted on the permanent masking graphic such that the second graphic is shielded from liquid communication with the absorbent assembly.

23. An absorbent article comprising:
an outer cover having an interior surface and an opposite exterior surface;
an absorbent assembly disposed on the interior surface;
a first graphic disposed on the outer cover and in liquid communication with the absorbent assembly, the first graphic comprising a liquid soluble composition;
a second graphic disposed on the outer cover and comprising a liquid soluble composition; and
a permanent masking graphic disposed on the outer cover at least partially peripherally surrounding the first graphic, the absorbent article further comprising a liquid soluble masking graphic superposed on the first graphic.

24. An absorbent article comprising:

an outer cover having an interior surface and an opposite exterior surface;

an absorbent assembly disposed on the interior surface;

a first graphic disposed on the outer cover and in liquid communication with the absorbent assembly, the first graphic comprising a liquid soluble composition;

a second graphic disposed on the outer cover and comprising a liquid soluble composition; and a permanent masking graphic disposed on the outer cover at least partially peripherally surrounding the first graphic, wherein the outer cover comprises a liquid permeable outer layer and a liquid impermeable Inner layer, the first graphic is disposed on one surface of the inner layer that forms the interior surface of the outer cover, and the second graphic is disposed on an opposite surface of the inner layer.

25. An absorbent article comprising:

an outer cover having an interior surface and an opposite exterior surface;

an absorbent assembly disposed on the interior surface;

a first graphic disposed on the outer cover and in liquid communication with the absorbent assembly, the first graphic comprising a liquid soluble composition;

a second graphic disposed on the outer cover and comprising a liquid soluble composition; and a permanent masking graphic disposed on the outer cover at least partially peripherally surrounding the first graphic, wherein the outer cover is adhesively attached to the absorbent assembly in a windowpane pattern, and the region of the outer cover containing the first graphic is unadhered to the absorbent assembly.

26. An absorbent article comprising:

an outer cover having an interior surface and an opposite exterior surface;

an absorbent assembly disposed on the interior surface; and a liquid soluble fading graphic disposed on the outer cover and in liquid communication with the absorbent assembly, the fading graphic being disposed in a fading graphic region;

wherein the absorbent assemble is bonded to the outer cover in regions other than the fading graphic region, and wherein a region of the outer cover including the fading graphic and at least a centimeter peripherally surrounding the fading graphic is not bonded to the absorbent assembly.

* * * * *